(12) United States Patent
Lin et al.

(10) Patent No.: US 6,458,993 B1
(45) Date of Patent: Oct. 1, 2002

(54) CYANATE ESTERS HAVING FLAME RESISTANT PROPERTIES

(75) Inventors: Bor-Sheng Lin, Berkeley Heights, NJ (US); Michael James Amone, Carmel, NY (US)

(73) Assignee: Vantico Inc., Brewster, NY (US)

( * ) Notice: Subject to any disclaimer, the term of this patent is extended or adjusted under 35 U.S.C. 154(b) by 0 days.

(21) Appl. No.: 09/773,305

(22) Filed: Jan. 31, 2001

Related U.S. Application Data

(62) Division of application No. 09/267,585, filed on Mar. 12, 1999.

(51) Int. Cl.[7] ............................................. C07C 261/00
(52) U.S. Cl. ......................... 560/301; 528/97; 528/99; 528/119; 528/120; 528/211; 528/271; 528/363; 528/422
(58) Field of Search ............................. 560/301; 528/97, 528/99, 119, 120, 211, 271, 363, 422

(56) References Cited

U.S. PATENT DOCUMENTS

| | | | |
|---|---|---|---|
| 3,856,566 A | 12/1974 | Saunders | 427/117 |
| 3,994,949 A | 11/1976 | Meyer et al. | 560/301 |
| 4,107,442 A | 8/1978 | Quinn | 568/726 |
| 4,110,541 A | 8/1978 | Kinson | 568/725 |
| 4,117,018 A | 9/1978 | Cleveland et al. | 568/726 |
| 4,223,171 A | 9/1980 | Mark et al. | 568/726 |
| 4,839,442 A | * 6/1989 | Craig, Jr. | 528/422 |
| 4,904,760 A | 2/1990 | Gaku et al. | 528/422 |
| 4,988,780 A | 1/1991 | Das et al. | 525/504 |
| 5,109,078 A | 4/1992 | Das et al. | 525/504 |
| 5,149,863 A | 9/1992 | Shimp et al. | 560/301 |
| 5,360,887 A | 11/1994 | Tsunemi et al. | 528/97 |
| 5,714,419 A | 2/1998 | Choate | 442/136 |

FOREIGN PATENT DOCUMENTS

| | | |
|---|---|---|
| JP | 05339342 | 12/1993 |
| JP | 11012464 | 1/1999 |

OTHER PUBLICATIONS

S. Ising et al., "Flammability resistance of non–brominated cyanate ester resins", Int. Sampe Symp. Exhib. (1989), 34, pp. 1326–1335 (Chem. Abstract 112:218046).

L. Hamilton et al., "Photodegradation of high performance fibers", Text. Chem. Color. (194), 26(12), pp. 39–45 (Chem. Abstract 123:58610).

* cited by examiner

*Primary Examiner*—Gary Geist
*Assistant Examiner*—Taylor V Oh
(74) *Attorney, Agent, or Firm*—Kristin H. Neuman; James H. Shalek

(57) ABSTRACT

The present invention relates to novel aromatic cyanate ester compounds containing at least two rings linked by a group containing an unsaturated group. The present invention further relates to compositions and prepolymers of said novel aromatic cyanate ester compounds. The present invention further relates to a process for preparing said compounds and cured articles resulting from curable mixtures thereof.

16 Claims, No Drawings

CYANATE ESTERS HAVING FLAME RESISTANT PROPERTIES

This application is a division of 09/267,585 filed Mar. 12, 1999.

This invention relates to novel aromatic cyanate ester compounds having at least two rings linked by an unsaturated group containing member, prepolymers and compositions thereof, and processes for making the same. The compounds can be employed in adhesives, composites, laminates and molding compositions. The compounds and compositions thereof have particular utility for use in molded articles requiring flame-resistance, low peak heat release rates, such as interiors for aircraft and other transportation vehicles, and low total heat release rates without generating significant amounts of smoke.

BACKGROUND OF THE INVENTION

Phenolic cyanate esters have been described extensively in the art. U.S. Pat. No. 5,360,887, for example, describes a flame resistant thermosetting composition containing a monocyanate ester and a dicyanate ester of the formula

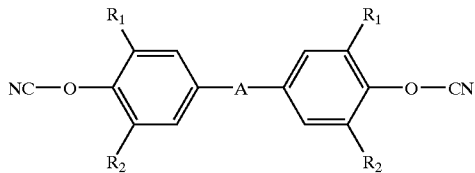

wherein the bridging member A can be a direct bond, methylene or mono- or disubstituted methylene with alkyl and/or an aryl group, or a five or six membered cycolalkylene, sulfonyl, thio, oxyl, carbonyl or xylylene. The teachings in U.S. Pat. No. 5,109,078 represent one of many teachings of cyanato-group containing phenolic resins of the formula:

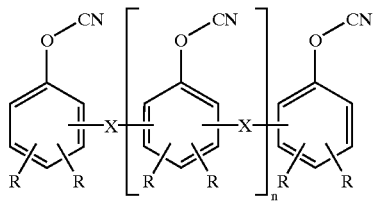

wherein X is a divalent organic radical, preferably a radical selected from the group consisting of: —CH2—, —CO—, —SO2—, (S)y,

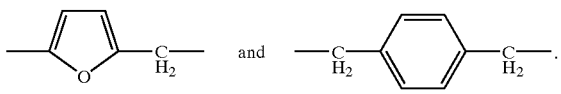

There is a need in the transportation industry, particularly for aircraft interiors, for molded polymeric components that exhibit very low peak heat release rates. Many cyanate esters exhibit good dielectric properties, water absorption and flame retardancy. However, all of the currently known cyanate esters fail to have heat release rates below 35 Joule/g-° K, more preferably below 10 Joule/g-° K. Low peak heat release rates can be attained using other high performance polymers such as polyphenylsulfone, polyamineimides, polybenzoimadazoles and polybenzoxazoles. All of the currently available polymers having relatively low peak heat release rates suffer from one or more disadvantages such as high cost of manufacture or challenging processing requirements. The present invention produces molded articles having the desired low peak heat release rate using cyanate ester compounds and compositions thereof.

SUMMARY OF THE INVENTION

The present invention relates, in a first aspect, to a compound represented by formula (I):

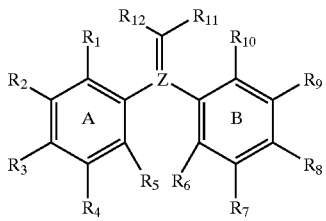

wherein
Z is $C_1$–$C_4$ alkylene group or a five or six membered cycolalkylene;

$R_1$, $R_5$, $R_6$ and $R_{10}$, independently of one another, are unsubstituted or halogen- or $C_1$–$C_3$alkyl-substituted $C_1$–$C_4$ alkyl that can be saturated or unsaturated, halogen, H, OCN, OH, $C_1$–$C_4$alkoxy, alkythio, mercaptan, nitro, —OCOR($C_1$–$C_3$alkyl), —NCOR ($C_1$–$C_3$alkyl), —COR, —NO$_2$, —NR'R", wherein R, R' and R" are H or $C_1$–$C_3$alkyl;

$R_2$, $R_4$, $R_7$ and $R_9$, independently of one another, are $C_1$–$C_4$alkyl, halogen, H, OCN, or OH, $C_1$–$C_4$alkoxy, alkythio, mercaptan, nitro, —OCOR($C_1$–$C_3$alkyl), —NCOR($C_1$–$C_3$alkyl), —COR, —NO$_2$, —NR'R", wherein R, R' and R" are H or $C_1$–$C_3$alkyl;

$R_3$ and $R_8$, independently of one another, are $C_1$–$C_4$alkyl, halogen H, OCN or OH, $C_1$–$C_4$alkoxy, alkythio, mercaptan, nitro, —OCOR($C_1$–$C_3$alkyl), —NCOR ($C_1$–$C_3$alkyl), —COR, —NO$_2$, —NR'R", wherein R, R' and R" are H or $C_1$–$C_3$alkyl; or $R_1$ and $R_2$ together and/or $R_2$ and $R_3$ together, and/or $R_9$ and $R_{10}$ together, and/or $R_8$ and $R_9$ together, independently of one another, form one or more aromatic rings or five or six membered cycloalkylene that can each be substituted with $C_1$–$C_4$alkyl or halogen;

$R_{11}$ and $R_{12}$, independently of one another are H, phenyl, $C_1$–$C_4$alkyl or halogen;

wherein at least one of aromatic rings A and B or at least one of the aromatic rings or the five or six membered ring formed by $R_1$ and $R_2$ and/or $R_2$ and $R_3$ and/or $R_9$ and $R_{10}$ and/or $R_8$ and $R_9$ is substituted by at least one cyanato group.

A preferred compound is characterized according to formula (I) above wherein Z is $C_1$–$C_2$alkylene; $R_1$ and $R_{10}$ are H; $R_2$, $R_4$, $R_7$ and $R_9$, independently of one another, are halogen, H, OCN, or OH; $R_3$, $R_5$, $R_6$ and $R_8$, independently of one another, are H, OCN or OH; $R_{11}$, and $R_{12}$ are halogen; and at least one of aromatic rings A and B is substituted by at least one cyanato group.

A particularly preferred compound is characterized according to formula (I) above wherein Z is $C_1$–$C_2$alkylene; $R_1$, $R_5$, $R_6$ and $R_{10}$ are H; $R_2$, $R_4$, $R_7$ and $R_9$, independently of one another, are halogen or H; $R_{11}$ and $R_{12}$ are halogen; and $R_3$ and $R_8$ are OCN. More preferably, $R_{11}$ and $R_{12}$ are chlorine or bromine. Most preferably, $R_{11}$ and $R_{12}$ are chlorine.

A further preferred compound is characterized according to formula (I) above wherein Z is methylene; $R_1$, $R_2$, $R_4$, $R_5$, $R_6$, $R_7$, $R_9$ and $R_{10}$ are H; $R_3$ and $R_8$ are OCN; and $R_{11}$ and $R_{12}$ are chlorine.

The present invention relates, in a second aspect, to a prepolymer mixture containing a cyclotrimerized reaction product of cyanate esters wherein at least one of said cyanate esters is the compound according to formula (I) above. Preferably, up to about 60% of the cyanato groups in the overall mixture are trimerized as a part of the cyclotrimerized reaction product. More particularly, about 10 to 40%, preferably, about 20 to 30% of the cyanato groups in the overall composition are trimerized as a part of the cyclotrimerized reaction product.

The present invention relates, in a further aspect, to a composition containing a) a compound according to formula (I) above or a cyclotrimerized reaction product thereof and b) a solvent or c) a monocyanate ester different from component a). Preferably, component c) is at least one halogen-substituted or unsubstituted aromatic monocyanate ester selected from naphthol cyanate, phenylphenol, chloronaphthol cyanate, chlorophenylphenol, dichloronaphthol cyanate, dichlorophenylphenol, bromonaphthol cyanate, bromophenylphenol, dibromonaphthol cyanate, dibromophenylphenol and mixtures thereof.

The present invention, in a further aspect, relates to a composition containing a) a compound according to formula (I) above or a cyclotrimerized reaction product thereof and b) a thermally curable monomer or oligomer other than a cyanate ester. Preferably, the thermally curable or reactive monomer or oligomer is selected from an epoxy, bismaleimide, polyimide, polyester, epoxy-acrylate, urethane-acrylate, diallyl phthalate, spiropyrane, phenolic resin and mixtures thereof.

The present invention, in a further aspect, relates to a composition containing a) at least 15%, preferably about 50 to 100%, more preferably about 60 to 99%, by weight of the overall composition of a compound according to formula (I) or a cyclotrimerized reaction product thereof with the balance of the composition optionally being at least one of components b) to g): b) solvent; c) additional mono- and polycyanato-group containing compounds; d) thermal curable or reactive compounds other than cyanate esters; e) cure accelerators; f) tougheners; and g) customary additives and fillers.

The present relates, in a still further aspect, to a process for preparing a cyanate ester comprising:

a) reacting at least one aromatic compound with a halogen substituted aldehyde, hemiacetal or acetal, in the presence of an acid to produce an aromatic compound having at least two rings according to formula (A)

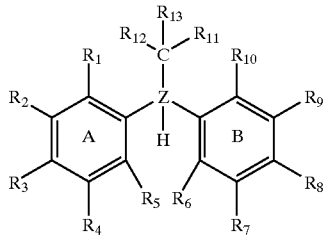

(A)

wherein
Z is $C_1$–$C_4$ alkylene group or a five or six membered cycolalkylene;
$R_1$, $R_5$, $R_6$ and $R_{10}$, independently of one another, are unsubstituted or halogen- or $C_1$–$C_3$alkyl-substituted $C_1$–$C_4$ alkyl that can be saturated or unsaturated, halogen, H, OCN, OH, $C_1$–$C_4$alkoxy, alkythio, mercaptan, nitro, —OCOR($C_1$–$C_3$alkyl), —NCOR ($C_1$–$C_3$alkyl), —COR, —$NO_2$, —NR'R", wherein R, R' and R" are H or $C_1$–$C_3$alkyl;

$R_2$, $R_4$, $R_7$ and $R_9$, independently of one another, are $C_1$–$C_4$alkyl, halogen, H, OCN, or OH, $C_1$–$C_4$alkoxy, alkythio, mercaptan, nitro, —OCOR($C_1$–$C_3$alkyl), —NCOR($C_1$–$C_3$alkyl), —COR, —$NO_2$, —NR'R", wherein R, R' and R" are H or $C_1$–$C_3$alkyl;

$R_3$ and $R_8$, independently of one another, are $C_1$–$C_4$alkyl, halogen H, OCN or OH, $C_1$–$C_4$alkoxy, alkythio, mercaptan, nitro, —OCOR($C_1$–$C_3$alkyl), —NCOR($C_1$–$C_3$alkyl), —COR, —$NO_2$, —NR'R", wherein R, R' and R" are H or $C_1$–$C_3$alkyl; or $R_1$ and $R_2$ together and/or $R_2$ and $R_3$ together, and/or $R_9$ and $R_{10}$ together, and/or $R_8$ and $R_9$ together, independently of one another, form one or more aromatic rings or five or six membered cycloalkylene that can each be substituted with $C_1$–$C_4$alkyl or halogen;

$R_{11}$, $R_{12}$ and $R_{13}$, independently of one another are H, phenyl, $C_1$–$C_4$alkyl or halogen with the proviso that at least one of the groups $R_{11}$, $R_{12}$, and $R_{13}$ must be halogen;

wherein at least one of aromatic rings A and B or at least one of the aromatic rings or the five or six membered ring formed by $R_1$ and $R_2$ and/or $R_2$ and $R_3$ and/or $R_9$ and $R_{10}$ and/or $R_8$ and $R_9$ is substituted by at least one hydroxyl group;

b) contacting the aromatic compound according to formula (A) with a basic compound to remove at least one halogen group from the carbon atom bonded to $R_{11}$, $R_{12}$ and $R_{13}$ and thereby producing an aromatic compound having at least two rings linked by a group containing an unsaturated group according to formula (B)

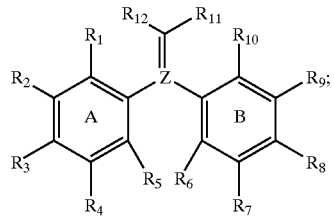

(B)

c) converting at least some of the hydroxyl groups of the aromatic compound according to formula (B) into cyanato-groups via reaction with a cyanogenhalide to produce an organic aromatic cyanate ester compound.

A preferred process employs a halogen-containing aldehyde, acetal or hemiacetal selected from fluoropropanal, fluoroacetaldehyde, bromopropanal, bromoacetaldehyde, chloroethanal, chloropropanal, chloroacetaldehyde, 2-chloro-1-ethoxy ethanol, 2-fluoro-1-ethoxy ethanol, 2-bromo-1-ethoxy ethanol, difluoropropanal, difluroacetaldehyde, dibromopropanal, dibromoacetaldehyde, dichloroethanal, dichloropropanal, dichloroacetaldehyde, 2,2-dichloro-1-ethoxy ethanol, 2,2-difluoro-1-ethoxy ethanol, 2,2-dibromo-1-ethoxy ethanol, trifluoropropanal, trifluoroacetaldehyde, tribromopropanal, tribromoacetaldehyde, trichloroethanal, trichloropropanal, trichloroacetaldehyde, 2,2,2-trichloro-1-ethoxy ethanol, 2,2,2-trifluoro-1-ethoxy ethanol, 2,2,2-tribromo-1-ethoxy ethanol and mixtures thereof. More preferably, the halogen-containing aldehyde, acetal or hemiacetal is selected from trichloroethanal, 2,2,2-trichloro-1-ethoxy ethanol and mixtures thereof.

A preferred process employs an aromatic compound that is to be reacted with the halogen-containing aldehyde, acetal or hemiacetal in step (a) that is selected from phenol, chlorophenol, dichlorophenol, cresol, xylenil, carvacol, thymol, naphthol, anthrol, phenanthrol, pyrocatechol, resorcinol, chlororesorcinol, dichlororesorcinol, hydroquinone, chlorohydroquinone, dichlorohydroquinone, trichlorohydroquinone, dinaphthol, chlorodinapthol, dichlorodinaphthol and mixtures thereof.

The process described above can advantageously be practiced such that the reaction mixture in step (a) further comprises a minor amount of a non-aromatic alcohol.

The preferred cyanogenhalide for practicing the process described above is selected from cyanogen chloride, cyanogen bromide and mixtures thereof.

The present invention, in a still further aspect, relates to a cured article resulting from a curable mixture comprising a compound according to formula (I) above or cyclotrimerized reaction product thereof having a peak heat release rate of less than about 10 Joule/g-° K as measured using a pyrolysis-combustion flow calorimeter developed by the Federal Aviation Administration or a peak heat release rate of less than 30, preferably 25 as measured according to the Ohio State University heat release test. The present further relates to a cured article resulting from a curable mixture comprising a compound according to formula (I) above or a cyclotrimerized reaction product thereof having a total heat release of less than about 3 KJoule/g. The cured articles do not generate significant amounts of smoke during combustion.

DETAILED DESCRIPTION OF THE INVENTION

The present invention is a flame resistant aromatic cyanate ester compound, prepolymers thereof, and compositions containing the same, articles of manufacture, and methods of making and using the same. The compound according to the present invention has a linking group containing an unsaturated group bridging at least two aromatic groups. More particularly, the compound can be represented by formula (I):

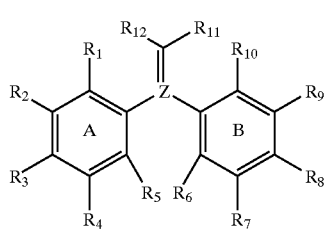

wherein

Z is $C_1$–$C_4$ alkylene group or a five or six membered cycolalkylene;

$R_1$, $R_5$, $R_6$ and $R_{10}$ independently of one another, are unsubstituted or halogen- or $C_1$–$C_3$alkyl-substituted $C_1$–$C_4$ alkyl that can be saturated or unsaturated, halogen, H, OCN, OH, $C_1$–$C_4$alkoxy, alkythio, mercaptan, nitro, —OCOR($C_1$–$C_3$alkyl), —NCOR ($C_1$–$C_3$alkyl), —COR, —NO$_2$, —NR'R", wherein R, R' and R" are H or $C_1$–$C_3$alkyl;

$R_2$, $R_4$, $R_7$ and $R_9$, independently of one another, are $C_1$–$C_4$alkyl, halogen, H, OCN, or OH, $C_1$–$C_4$alkoxy, alkythio, mercaptan, nitro, —OCOR($C_1$–$C_3$alkyl), —NCOR($C_1$–$C_3$alkyl), —COR, —NO$_2$, —NR'R", wherein R, R' and R" are H or $C_1$–$C_3$alkyl;

$R_3$ and $R_8$, independently of one another, are $C_1$–$C_4$alkyl, halogen H, OCN or OH, $C_1$–$C_4$alkoxy, alkythio, mercaptan, nitro, —OCOR($C_1$–$C_3$alkyl), —NCOR ($C_1$–$C_2$alkyl), —COR, —NO$_2$, —NR'R", wherein R, R' and R" are H or $C_1$–$C_3$alkyl; or $R_1$ and $R_2$ together and/or $R_2$ and $R_3$ together, and/or $R_9$ and $R_{10}$ together, and/or $R_8$ and $R_9$ together, independently of one another, form one or more aromatic rings or five or six membered cycloalkylene that can each be substituted with $C_1$–$C_4$alkyl or halogen;

$R_{11}$ and $R_{12}$, independently of one another are H, phenyl, $C_1$–$C_4$alkyl or halogen;

wherein at least one of aromatic rings A and B or at least one of the aromatic rings or the five or six membered ring formed by $R_1$ and $R_2$ and/or $R_2$ and $R_3$ and/or $R_9$ and $R_{10}$ and/or $R_8$ and $R_9$ is substituted by at least one cyanato group.

In a more preferred compound, Z is $C_1$–$C_2$alkylene, $R_1$ and $R_{10}$ are H; $R_2$, $R_4$, $R_7$ and $R_9$, independently of one another, are halogen, H, OCN, or OH; $R_3$ and $R_8$, independently of one another, are H, OCN or OH; $R_5$ and $R_6$, independently of one anther, are H, OCN or OH; and $R_{11}$ and $R_{12}$ are halogen, wherein at least one of aromatic rings A and B is substituted by at least one cyanato group. In a particularly preferred compound, Z is $C_1$–$C_2$alkylene, $R_1$, $R_5$, $R_6$ and $R_{10}$ are H; $R_2$, $R_4$, $R_7$ and $R_9$, independently of one another, are halogen or H; $R_3$ and $R_8$ are OCN; and $R_{11}$ and $R_{12}$ are halogen. A most preferred compound is characterized by Z being methylene, $R_1$, $R_2$, $R_4$, $R_5$, $R_6$, $R_7$, $R_9$ and $R_{10}$ being H; $R_3$ and $R_8$ being a cyanato group and $R_{11}$ and $R_{12}$ being chlorine.

The novel compound is prepared by reacting, in a first reaction, an aromatic compound substituted with a mono-, di- or tri-halogen containing aldehyde, acetal or hemiacetal or corresponding alcohol, in the presence of an acid, preferably a highly acidic environment having a pH of less than about 3, to produce an aromatic compound containing at least two rings linked by the halogen-substituted residue of the aldehyde, acetal or hemiacetal.

In a second reaction, the resulting aromatic compound is contacted by a basic compound, such as potassium hydroxide, and an organic non-polar solvent, such as methanol, to remove at least one halogen group to produce an aromatic compound wherein the at least two rings are linked by a group containing an unsaturated group. The aforementioned reactions are described in greater detail in U.S. Pat. Nos. 3,856,566, 4,110,541, and 4,117,018, which are each incorporated herein by reference. In a third reaction, at least some of the hydroxyl groups of the aromatic compound resulting from the second reaction are converted into cyanato-groups via reaction with a cyanogenhalide, such as cyanogen chloride or cyanogen bromide, via a known reaction as described in U.S. Pat. No. 5,149,863 (which is incorporated herein by reference) to produce the desired final product. The resulting product can be used as is or recrystallized in purer form. The amount of cyanogenhalide should be sufficient to react with all of the hydroxyl groups of the aromatic compound resulting from the second reaction though greater or lesser than stoichiometric amounts can be employed.

Suitable aromatic compounds for this invention contain one or more aromatic rings having at least one hydroxyl group. The aromatic rings can be further substituted with alkyl and/or halogen groups. Examples of suitable aromatic compounds are phenol, phenyl phenol, cresol, xylenil, carvacol, thymol, naphthol, disubstituted naphthol, anthrol, phenanthrol, pyrocatechol, resorcinol, hydroquinone, and bicyclic hydroxyl-containing compounds linked by alkylene, carbonyl, oxyl, and/or sulfonyl groups and halogenated, such as bromine, fluorine and chlorine, corresponding compounds. It is anticipated that halogen substitution would improve the flame retardancy of molded articles resulting from such halogenated compounds and compositions thereof. Mixtures of said aromatic compounds can be used as well as mixtures with minor amounts of non-aromatic alcohols. Phenol is a particularly preferred aromatic compound for use herein.

Suitable halogen-containing aldehydes, acetals and hemiacetals include mono- and polyhalogenated compounds, such as fluoropropanal or fluoroacetaldehyde, bromopropanal or bromoacetaldehyde, chloroethanal, chloropropanal or chloroacetaldehyde, 2-chloro-1-ethoxy ethanol, 2-fluoro-1-ethoxy ethanol, 2-bromo-1-ethoxy ethanol, difluoropropanal or difluroacetaldehyde, dibromopropanal or dibromoacetaldehyde, dichloroethanal, dichloropropanal or dichloroacetaldehyde, 2,2-dichloro-1-ethoxy ethanol, 2,2-difluoro-1-ethoxy ethanol, 2,2-dibromo-1-ethoxy ethanol, trifluoropropanal or trifluoroacetaldehyde, tribromopropanal or tribromoacetaldehyde (bromal), trichloroethanal, trichloropropanal or trichloroacetaldehyde (chloral), 2,2,2-trichloro-1-ethoxy ethanol, 2,2,2-trifluoro-1-ethoxy ethanol, 2,2,2-tribromo-1-ethoxy ethanol. Trichloroethanal and 2,2, 2-trichloro-1-ethoxy ethanol are particularly preferred.

A particularly preferred reaction sequence is exemplified below:

The novel compound described above forms a solid resin having a softening point in the range of 70 to 80° C. The inventive compound described above can be used alone or combined with other mono- and polycyanato-group containing compounds to form thermosetting resin compositions. The additional cyanato-group containing compounds can be halogenated in order to improve flame retardancy. The additional cyanato-group containing compounds can be combined with the inventive compound described above in order to modify the glass transition temperature and improve processing of the overall composition provided that the overall objective is achieved of obtaining a molded article having low peak heat release characteristics. Applicants have found, for example, that the addition of aromatic monocyanates, such as naphthol cyanate, phenylphenol cyanate and the monocyanate of the inventive compounds disclosed herein, preferably up to about 40% by weight depending upon the type of selected aromatic cyanate reduces the glass transition temperature of the overall thermosetting composition without significantly increasing the peak heat release rate of the resulting molded articles and impacting mechanical properties.

The inventive compound described above can also be combined with other thermal curable monomers and reactants, such as epoxies, bismaleimides, polyimides, polyesters, epoxy-acrylates, urethane-acrylates, diallyl phthalates, spiropyrane, and phenol provided the molded article retains the desired low heat release characteristics. The composition can also contain a curing catalyst, such as imidazole compounds, tertiary amines or organometallic compounds. Organometallic compounds such as cobalt

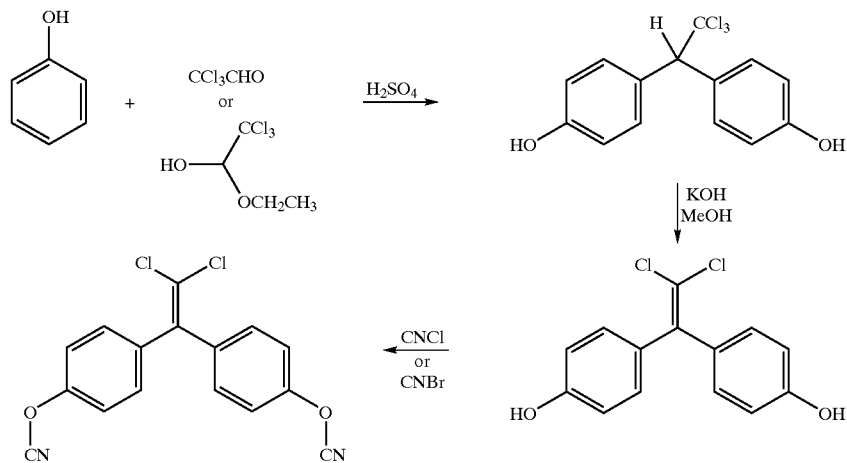

The novel compound described above forms, in conventional manner, an aromatic triazine network upon heating and/or in the presence of a curing agent. Typical curing conditions are from 120° C. to 250° C. at atmospheric to 500 psi pressure for 0.1 to 1 hour depending upon the sample size, temperatures, and pressures. The curing reaction is known as cyclotrimerization. At least three moles of cyanate ester monomer described above are required to produce one mole of cyclotrimerized prepolymer product. A composition containing the novel compound described above can be cyclotrimerized in conventional fashion to produce a prepolymer wherein up to about 60% of the cyanato groups in the overall composition have been trimerized. More preferably, the prepolymer is characterized by having about 10 to 40%, more preferably about 20 to 30% of the cyanato groups trimerized.

octanate, zinc octanate, cobalt naphthalenate, or zinc naphthenate are preferred. The curing reaction can also be further accelerated by the addition of small amounts of phenols, such as bisphenol A, bisphenol F, bisphenol S, or p-nonylphenol. The composition can also further contain a filler such as alumina, aluminum hydroxide, antimony tri- or pentaoxide, zinc oxide, titanium dioxide, silica powder, quartz powder, glass powder, ceramic microballons or mixtures thereof.

A preferred thermosetting composition or resin varnish contains at least 30%, more preferably 50 to 100%, most preferably 60 to 99% by weight of the inventive compound and/or its corresponding prepolymer with the balance being solvent, additional mono-and polycyanato-group containing compounds, thermal curable or reactive compounds other than cyanate esters, cure accelerators and customary additives and fillers. Suitable solvents include ketones, such as methyl ethyl ketone, methyl isobutyl ketone, aromatic hydrocarbons, such as toluene or xylene, ethers, such as dioxane, tetrahydrofuran or ethylene glycol monomethyl ether, alcohols, such as methanol, ethanol, isopropyl alcohol, amides, such as dimethylformamide or dimethylacetamide and mixtures thereof. Aromatic hydrocarbons and ketones are preferred.

For casting applications, a thermosetting composition described above is heated to a molten state to produce a prepolymer composition before casting into a mold, and then allowed to cure at an elevated temperature. For bonding applications, a resin varnish or molten prepolymer composition is applied to the surfaces to be bonded, and then allowed to cure under heat and pressure. Prepregs are produced by impregnating a suitable substrate with a resin varnish containing the inventive compound and drying the impregnated substrate. The impregnation apparatus can be of conventional design. Examples of substrates used in the preparation of prepregs include carbon fiber, glass fiber substrates, such as glass cloth or glass non-woven fabric, cellulosic substrates, such as kraft paper or cotton linter paper, synthetic fiber fabric such as aramide cloth or aramide nonwoven fabric. Composite laminates can be produced using different types of substrates in combination. The compounds and compositions disclosed herein can be utilized to produce aircraft interior section in known fashion, such as the interiors disclosed in U.S. Pat. No. 5,714,419, assigned on its face to Fiberite, Inc., which is incorporated herein by reference.

Microcombustion data for molded articles containing the inventive compounds were obtained using a pyrolysis-combustion flow calorimeter developed by the Federal Aviation Administration ("FAA"). In the test, 1 to 5 mg sample is placed in a 10-mm-long by 2.5-mm outside diameter quartz tube. A linear 10° C./second heating rate is used. The pyrolysis products are swept from the pyrolyzer by flowing nitrogen gas stream through a heated transfer line and mixed with excess oxygen prior to entering a high-temperature furnace to force complete combustion of the pyrolyzate. The heat release by combustion is calculated from the oxygen consumption using a universal value of 13.1 kJ of heat released per gram of diatomic oxygen consumed. The data of peak heat release rate and total heat release are obtained from the calorimeter on triplicate samples of each material measured.

The flammability resistance for the resin was also measured according to the Ohio State University heat release test (OSU test). This test measures the amount of heat evolved in a period of 2 minutes (C) as well as the rare of heat evolution at the peak (B) when a given test sample is exposed to radiation under specified conditions. OSU test results in a curve of heat evolution versus time. The rate of heat is increased at specified conditions according to the Federal Aviation Administration (FAA). This corresponds to the impingement of a sample at rate of 3.5 watts/cm$^2$. The volatiles are completely burnt by a small flame and the heat evolved is recorded as a function of time. Glass fabric does not contribute to heat evolution.

Several examples are set forth below to illustrate the nature of the invention and method for carrying it out. However, the invention should not be considered as being limited to the details thereof. All parts are in parts by weight unless otherwise indicated.

EXAMPLE 1

1,1-dichloro-2,2-bis(4-cyanatophenyl)ethylene is prepared as follows. A 4-necked 3-L flask, equipped with a mechanical stirrer, a nitrogen inlet, and thermometer, is charged with 83% sulfuric acid (640 g). To this sulfuric acid, phenol (354 g) is added at 20° C. Chloral (200 g) in an additional funnel is added dropwise to the phenolic stirring mixture. The reaction temperature is maintained below 30° C. After the addition, the mixture is allowed to stir at room temperature for 18 hours, before water (640 g) is added. The resulting mixture is filtered and washed with more water to afford 1,1,1-trichloro-2,2-bis(4-hydroxyphenyl)ethane (423 g) as white solids.

A 4-necked 5-liter flask, equipped with a mechanical stirrer, a thermometer, and a condenser, is charged with methanol (800 g). Potassium hydroxide (440 g) is added in portions to the methanol solution. After the addition, the solution is cooled to 20° C. To this stirring solution, 1,1,1-trichloro-2,2-bis(4-hydroxyphenyl)ethane (420 g) is added in portions. The reaction temperature is kept below 40° C. After the addition, the temperature is raised to 50° C. and maintained for 2.5 hours. The reaction mixture is cooled to 20° C. and neutralized with 25% HCl solution. After the neutralization, the mixture is heated to reflux and water (480 g) is added. The mixture is allowed to cool to the room temperature. The precipitates are filtered and dried to afford 1,1-dichloro-2,2-bis(4-hydroxyphenyl)ethene as white solids with slight tan color.

A 4-necked 5-L flask, equipped with a mechanical stirrer, a thermometer, and an additional funnel, is charged with methyl isobutyl ketone (1500 g), 1,1-dichloro-2,2-bis(4-hydroxyphenyl)ethene (320 g), and cyanogen bromide (270 g). The resulting solution is cooled to −20° C. with a dry ice/acetone bath. To the stirring solution, triethylamine (240 g) in the additional funnel is added dropwise. The reaction temperature is maintained below −20° C. After the addition, the resulting mixture is allowed to warm up to 0° C. and quenched with dilute HCl aqueous solution. The organic layer is washed further with water a few times and concentrated under vacuum to afford 370 g of amber liquid, which solidifies as light tan color solids.

EXAMPLE 2

1,1-dibromo-2,2-bis(4-cyanatophenyl)ethylene is prepared as follows. A 4-necked 3-L flask, is equipped with a mechanical stirrer, a nitrogen inlet, and thermometer, is charged with 83% sulfuric acid (640 g) and phenol (354 g). To the resulting milky mixture, tribromoacetaldehyde (380 g) in an additional funnel is added dropwise. The reaction temperature is maintained below 30° C. After the addition, the mixture is allowed to stir at the room temperature for 18 hours, before water (640 g) is added. The resulting mixture is filtered and washed with more water to afford 1,1,1-tribromo-2,2-bis(4-hydroxyphenyl)ethane.

A 4-necked 5-liter flask, equipped with a mechanical stirrer, a thermometer, and a condenser, is charged with methanol (800 g). Potassium hydroxide (440 g) is added in portions to the methanol solution. After the addition, the solution is cooled to 20° C. To this stirring solution, 1,1,1-tribromo-2,2-(4-hydroxyphenyl)ethane (420 g) is added in portions. The reaction temperature is kept below 40° C. After the addition, the temperature is raised to 50° C. and kept for 2 hours. The reaction mixture is cooled to room temperature and neutralized with 25% HCl solution. After the neutralization, the mixture is heated to reflux and water is added. The mixture is allowed to cool to the room temperature. The precipitates formed are filtered and dried to afford 1,1-dibromo-2,2-bis(4-hydroxyphenyl)ethene.

A 4-necked 5-L flask, equipped with a mechanical stirrer, a thermometer, and an additional funnel, is charged with methyl isobutyl ketone (1500 g), 1,1-dibromo-2,2-bis(4-hydroxyphenyl)ethene (420 g), and cyanogen bromide (270 g). The resulting solution is cooled to −20° C. with a dry ice/acetone bath. To the stirring solution, triethylamine (240 g) in the additional funnel is added dropwise. The reaction temperature is maintained below −20° C. After the addition, the resulting mixture is allowed to warm up to 0° C. and quenched with dilute HCl aqueous solution. The organic layer is washed further with water several times and concentrated under vacuum to afford the desired product.

The following compounds are made in accordance with the procedures set forth in example 1.

| NO. | Aromatic Group | Major Product(s) |
|---|---|---|
| 11 | cresol | 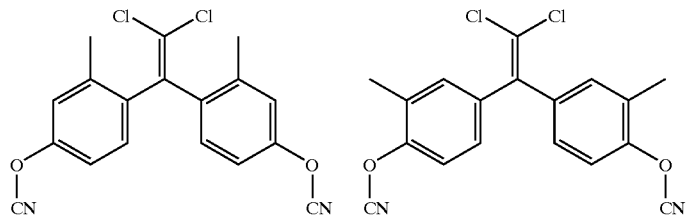 |
| 12 | xylenil | 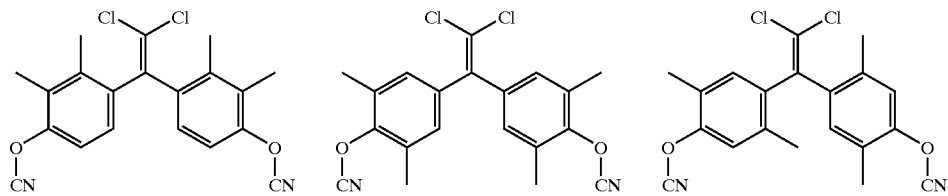 |
| 13 | carvacol | 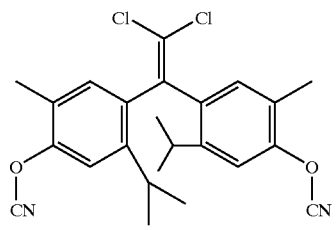 |
| 14 | thymol | 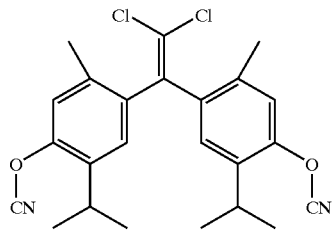 |
| 15 | naphthol | 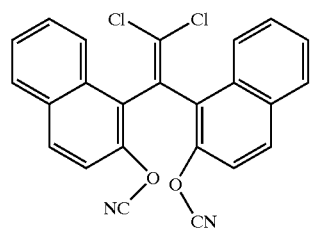 |
| 16 | anthrol | 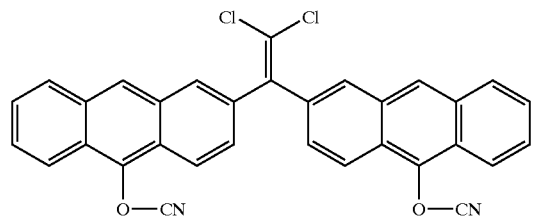 |

-continued
| 17 | phenanthrol | 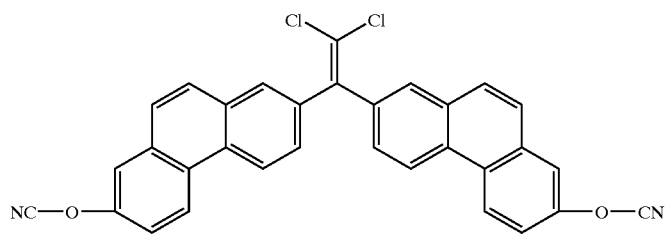 |
| 18 | pyrocatechol | 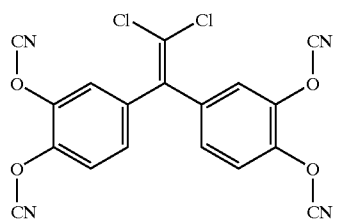 |
| 19 | hydro quinone | 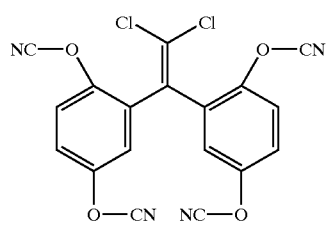 |
| 20 | resorcinol | 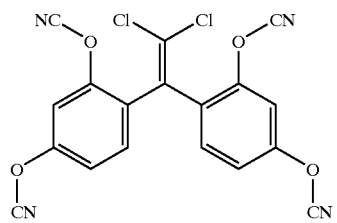 |
| 21 | chloro phenol | 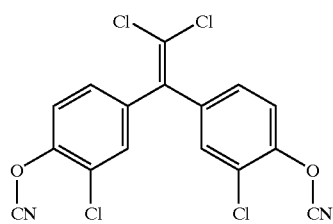 |
| 22 | dichloro phenol | 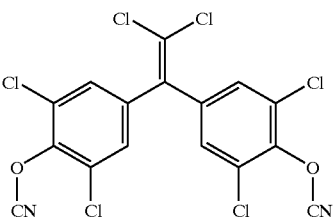 |

| | | |
|---|---|---|
| 23 | chloro hydroquinone | 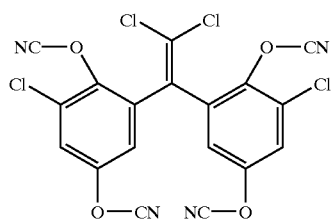 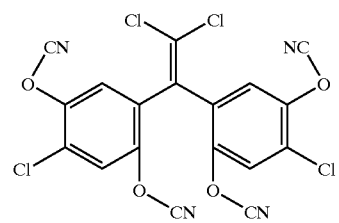 |
| 24 | 2,6-dichloro hydroquinone | 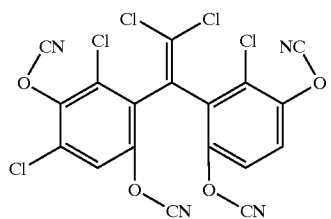 |
| 25 | 2,5-dichloro hydroquinone | 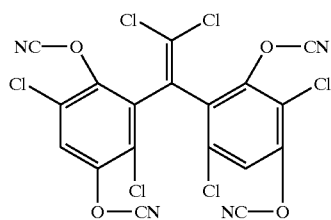 |
| 26 | 2,3,6-trichlorohydro quinone | 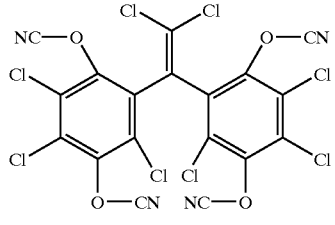 |
| 26 | 4-chloro resorcinol | 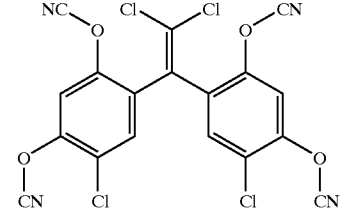 |
| 27 | 4,6-dichloro resorcinol | 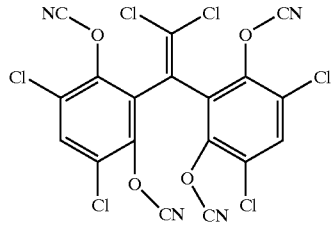 |

Application Example 1.

In an aluminum dish, 12 g of the resin of example 1 is mixed with 12 mg of 6% manganese octoate solution in hexane at 100° C. The resulting mixture is cured at 160° C. for 1 hour and 220° C. for 2 hours. The cured resin from example 1 and comparative materials are studied for their heat release rate with the microcalorimeter developed by the Technical Center of FAA. Comp. 1a is cured phenol formaldehyde resin. Comp. 1b is cured cyanate ester resin, PT-30.

The test was done on each sample in triplicate. The average values are listed in Table 1.

TABLE 1

Results of Micro Heat Release Study

| | Peak Heat Release Rate Joule/g-° K. | Total Heat Release KJoule/g |
|---|---|---|
| Ex. 1 | 8.0 | 1.8 |
| Comp. 1a | 41.9 | 6.2 |
| Comp. 1b | 59.2 | 7.2 |

Application Example 2

A number of ⅛ inch composite using glass or carbon fabric and resin are prepared. A predetermined size of glass or carbon fabric is uniformly coated with 60% wt solution of resin in acetone. The resin is prepared from the product from example 1 and 0.1% of a 6% solution of manganese octoate in hexane. The prepreg are dried and 1 ply of the prepreg is stacked on each side of ⅛ inch Nomex honeycomb and the sandwich panel is cured in a hot press. Curing is carried out at 160° C. for 1 hour and 220° C. for 2 hours. The cured laminates are weighed and the resin content is determined to be about 35%. Ex. 2a is the sandwich panel with glass fabric and ex. 2b is the sandwich panel with carbon fabric. Comp. 2a is made from phenol formaldehyde resin and glass fabric. Comp. 2b is made from phenol formaldehyde resin and carbon fabric. The OSU test is carried out on each sample in triplicate. The average of three value is shown in

TABLE 2

OSU Test Results

| | Peak Heat Release Rate KW/m² | Total Heat Release KW/m²-min |
|---|---|---|
| Ex. 2a | 20.7 | 19.6 |
| Ex. 2b | 19.8 | 19.2 |
| Comp. 2a | 53.2 | 44.4 |
| Comp. 2b | 50.6 | 41.8 |

Preferred embodiments of the present invention relating to novel aromatic cyanate esters, compositions thereof and methods for using the same have been described above. Those skilled in the art having the benefit of the teachings presented in the foregoing will recognize modifications and other embodiments. Therefore, it is understood that the invention is not limited to the specific embodiments disclosed herein, and that modifications and other embodiments are intended to be within the scope of the appended claims.

I claim:

1. A prepolymer mixture comprising a cyclotrimerized reaction product of cyanate esters wherein at least one of said cyanate esters is a compound represented by formula (I):

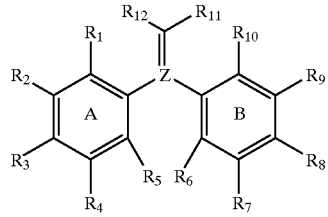

wherein

Z is $C_1$–$C_4$ alkylene group or a five or six membered cycolalkylene;

$R_1$, $R_5$, $R_6$, and $R_{10}$, independently of one another, are unsubstituted or halogen- or $C_1$–$C_3$alkyl-substituted $C_1$–$C_4$ alkyl that can be saturated or unsaturated, halogen, H, OCN, OH, $C_1$–$C_4$alkoyxy, alkythio, mercaptan, nitro, —OCOR($C_1$–$C_3$alkyl), —NCOR ($C_1$–$C_3$alkyl), —COR, —NO$_2$, —NR'R", wherein R, R' and R" are H or $C_1$–$C_3$alkyl;

$R_2$, $R_4$, $R_7$ and $R_9$, independently of one another, are $C_1$–$C_4$alkyl, halogen, H, OCN, or OH, $C_1$–$C_4$alkoxy, alkythio, mercaptan, nitro, —OCOR($C_1$–$C_3$alkyl), —NCOR($C_1$–$C_3$alkyl), —COR, —NO$_2$, —NR'R", wherein R, R' and R" are H or $C_1$–$C_3$alkyl;

$R_3$ and $R_8$, independently of one another, are $C_1$–$C_4$alkyl, halogen H, OCN or OH, $C_1$–$C_4$alkoxy, alkythio, mercaptan, nitro, —OCOR($C_1$–$C_3$alkyl), —NCOR ($C_1$–$C_3$alkyl), —COR, —NO$_2$, —NR'R", wherein R, R' and R" are H or $C_1$–$C_3$alkyl; or $R_1$ and $R_2$ together and/or $R_2$ and $R_3$ together, and/or $R_9$ and $R_{10}$ together, and/or $R_8$ and $R_9$ together, independently of one another, form one or more aromatic rings or five or six membered cycloalkylene that can each be substituted with $C_1$–$C_4$alkyl or halogen;

$R_{11}$ and $R_{12}$, independently of one another are H, phenyl, $C_1$–$C_4$alkyl or halogen;

wherein at least one of aromatic rings A and B or at least one of the aromatic rings or the five or six membered ring formed by $R_1$ and $R_2$ and/or $R_2$ and $R_3$ and/or $R_9$ and $R_{10}$ and/or $R_8$ and $R_9$ is substituted by at least one cyanato group.

2. A prepolymer mixture according to claim 1 wherein up to about 60% of the cyanato groups in the overall composition are trimerized as a part of the cyclotrimerized reaction product.

3. A prepolymer mixture according to claim 1 wherein about 10 to 40% of the cyanato groups in the overall composition are trimerized as a part of the cyclotrimerized reaction product.

4. A prepolymer mixture according to claim 1 wherein about 20 to 30% of the cyanato groups in the overall composition are trimerized as a part of the cyclotrimerized reaction product.

5. A composition comprising
a) a compound represented by formula (I):

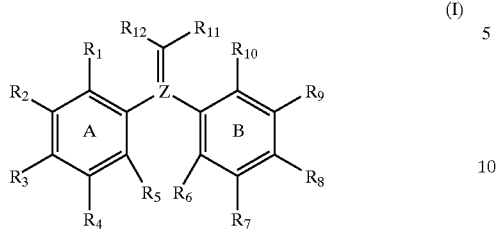

wherein
Z is $C_1$–$C_4$ alkylene group or a five or six membered cycolalkylene;
$R_1$, $R_5$, $R_6$ and $R_{10}$ independently of one another, are unsubstituted or halogen- or $C_1$–$C_3$alkyl-substituted $C_1$–$C_4$ alkyl that can be saturated or unsaturated, halogen, H, OCN, OH, $C_1$–$C_4$alkoxy, alkythio, mercaptan, nitro, —OCOR($C_1$–$C_3$alkyl), —NCOR ($C_1$–$C_3$alkyl), —COR, —NO$_2$, —NR'R", wherein R, R' and R" are H or $C_1$–$C_3$alkyl;
$R_2$, $R_4$, $R_7$ and $R_9$ independently of one another, are $C_1$–$C_4$alkyl, halogen, H, OCN, or OH, $C_1$–$C_4$alkoxy, alkythio, mercaptan, nitro, —OCOR($C_1$–$C_3$alkyl), —NCOR($C_1$–$C_3$alkyl), —COR, —NO$_2$, —NR'R", wherein R, R' and R" are H or $C_1$–$C_3$alkyl;
$R_3$ and $R_8$, independently of one another, are $C_1$–$C_4$alkyl, halogen H, OCN or OH, $C_1$–$C_4$alkoxy, alkylthio, mercaptan, nitro, —OCOR($C_1$–$C_3$alkyl), —NCOR($C_1$–$C_3$alkyl, —COR, —NO$_2$, —NR'R", wherein R, R' and R" are H or $C_1$–$C_3$alkyl; or
$R_1$ and $R_2$ together and/or $R_2$ and $R_3$ together, and/or $R_9$ and $R_{10}$ together, and/or $R_8$ and $R_9$ together, independently of one another, form one or more aromatic rings or five or six membered cycloalkylene that can each be substituted with $C_1$–$C_4$alkyl or halogen;
$R_{11}$ and $R_{12}$, independently of one another are H, phenyl, $C_1$–$C_4$alkyl or halogen;
wherein at least one of aromatic rings A and B or at least one of the aromatic rings or the five or six membered ring formed by $R_1$, and $R_2$ and/or $R_2$ and $R_3$ and/or $R_9$ and $R_{10}$ and/or $R_8$ and $R_9$ is substituted by at least one cyanato group,
or a cyclotrimerized reaction product of cyanate esters wherein at least one of said cyanate esters is said compound of formula (I) and
b) a solvent.

6. A composition comprising
a) a compound represented by formula (I):

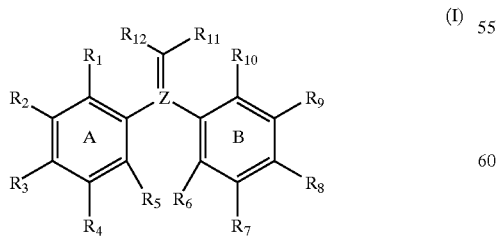

wherein
Z is $C_1$–$C_4$ alkylene group or a five or six membered cycolalkylene;
$R_1$, $R_5$, $R_6$ and $R_{10}$, independently of one another, are unsubstituted or halogen- or $C_1$–$C_3$alkyl-substituted $C_1$–$C_4$ alkyl that can be saturated or unsaturated, halogen, H, OCN, OH, $C_1$–$C_4$alkoxy, alkythio, mercaptan, nitro, —OCOR($C_1$–$C_3$alkyl), —NCOR ($C_1$–$C_3$alkyl), —COR, —NO$_2$, —NR'R", wherein R, R' and R" are H or $C_1$–$C_3$alkyl;
$R_2$, $R_4$, $R_7$ and $R_9$ independently of one another, are $C_1$–$C_4$alkyl, halogen, H, OCN, or OH, $C_1$–$C_4$alkoxy, alkythio, mercaptan, nitro, —OCOR($C_1$–$C_3$alkyl), —NCOR($C_1$–$C_3$alkyl), —COR, —NO$_2$, —NR'R", wherein R, R' and R" are H or $C_1$–$C_3$alkyl;
$R_3$ and $R_8$, independently of one another, are $C_1$–$C_4$alkyl, halogen H, OCN or OH, $C_1$–$C_4$alkoxy, alkythio, mercaptan, nitro, —OCOR($C_1$–$C_3$alkyl), —NCOR($C_1$–$C_3$alkyl), —COR, —NO$_2$, —NR'R", wherein R, R' and R" are H or $C_1$–$C_3$alkyl; or
$R_1$ and $R_2$ together and/or $R_2$ and $R_3$ together, and/or $R_9$ and $R_{10}$ together, and/or $R_8$ and $R_9$ together, independently of one another, form one or more aromatic rings or five or six membered cycloalkylene that can each be substituted with $C_1$–$C_4$alkyl or halogen;
$R_{11}$ and $R_{12}$, independently of one another are H, phenyl, $C_1$–$C_4$alkyl or halogen;
wherein at least one of aromatic rings A and B or at least one of the aromatic rings or the five or six membered ring formed by $R_1$ and $R_2$ and/or $R_2$ and $R_3$ and/or $R_9$ and $R_{10}$ and/or $R_8$ and $R_9$ is substituted by at least one cyanato group,
or a cyclotrimerized reaction product of cyanate esters wherein at least one of said cyanate esters is said compound of formula (I) and
b) a monocyanate ester different from component a).

7. A composition according to claim 6 wherein component b) is at least one halogen-substituted or unsubstituted aromatic monocyanate ester.

8. A composition according to claim 7 wherein component b) is selected from naphthol cyanate, phenylphenol, chloronaphthol cyanate, chlorophenylphenol, dichloronaphthol cyanate, dichlorophenylphenol, bromonaphthol cyanate, bromophenylphenol, dibromonaphthol cyanate, dibromophenylphenol and mixtures thereof.

9. A composition comprising
a) a compound represented by formula (I):

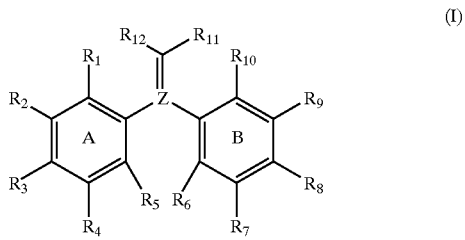

wherein
Z is $C_1$–$C_4$ alkylene group or a five or six membered cycolalkylene;
$R_1$, $R_5$, $R_6$ and $R_{10}$, independently of one another, are unsubstituted or halogen- or $C_1$–$C_3$alkyl-substituted $C_1$–$C_4$alkyl that can be saturated or unsaturated, halogen, H, OCN, OH, $C_1$–$C_4$alkoxy, alkythio, mercaptan, nitro, —OCOR($C_1$–$C_3$alkyl), —NCOR ($C_1$–$C_3$alkyl), —COR, —NO$_2$, —NR'R", wherein R, R' and R" are H or $C_1$–$C_3$alkyl;

$R_2$, $R_4$, $R_7$ and $R_9$ independently of one another, are $C_1$–$C_4$alkyl, halogen, H, OCN, or OH, $C_1$–$C_4$alkoxy, alkythio, mercaptan, nitro, —OCOR($C_1$–$C_3$alkyl), —NCOR($C_1$–$C_3$alkyl), —COR, —NO$_2$, —NR'R", wherein R, R' and R" are H or $C_1$–$C_3$alkyl;

$R_3$ and $R_8$, independently of one another, are $C_1$–$C_4$alkyl, halogen H, OCN or OH, $C_1$–$C_4$alkoxy, alkythio, mercaptan, nitro, —OCOR($C_1$–$C_3$alkyl), —NCOR($C_1$–$C_3$alkyl), —COR, —NO$_2$, —NR'R", wherein R, R' and R" are H or $C_1$–$C_3$alkyl; or $R_1$ and $R_2$ together and/or $R_2$ and $R_3$ together, and/or $R_9$ and $R_{10}$ together, and/or $R_8$ and $R_9$ together, independently of one another, form one or more aromatic rings or five or six membered cycloalkylene that can each be substituted with $C_1$–$C_4$alkyl or halogen;

$R_{11}$ and $R_{12}$, independently of one another are H, phenyl, $C_1$–$C_4$alkyl or halogen;

wherein at least one of aromatic rings A and B or at least one of the aromatic rings or the five or six membered ring formed by $R_1$ and $R_2$ and/or $R_2$ and $R_3$ and/or $R_9$ and $R_{10}$ and/or $R_8$ and $R_9$ is substituted by at least one cyanato group, or a cyclotrimerized reaction product of cyanate esters wherein at least one of said cyanate esters is said compound of formula (I) and b) a thermally curable monomer or oligomer other than a cyanate ester.

10. A composition according to claim 9 wherein the thermally curable or reactive monomer or oligomer is selected from an epoxy, bismaleimide, polyimide, polyester, epoxy-acrylate, urethane-acrylate, diallyl phthalate, spiropyrane, phenolic resin and mixtures thereof.

11. A composition comprising a) at least 15% by weight of the overall composition of a compound represented by formula (I):

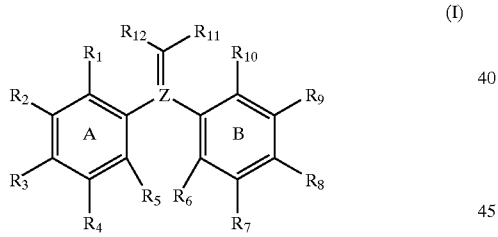

(I)

wherein

Z is $C_1$–$C_4$ alkylene group or a five or six membered cycolalkylene;

$R_1$, $R_5$, $R_6$, and $R_{10}$, independently of one another, are unsubstituted or halogen- or $C_1$–$C_3$alkyl-substituted $C_1$–$C_4$ alkyl that can be saturated or unsaturated, halogen, H, OCN, OH, $C_1$–$C_4$alkoxy, alkythio, mercaptan, nitro, —OCOR($C_1$–$C_3$alkyl), —NCOR ($C_1$–$C_3$alkyl), —COR, —NO$_2$, —NR'R", wherein R, R' and R" are H or $C_1$–$C_3$alkyl;

$R_2$, $R_4$, $R_7$ and $R_9$ independently of one another, are $C_1$–$C_4$alkyl, halogen, H, OCN, or OH, $C_1$–$C_4$alkoxy, alkythio, mercaptan, nitro, —OCOR($C_1$–$C_3$alkyl), —NCOR($C_1$–$C_3$alkyl), —COR, —NO$_2$, —NR'R", wherein R, R' and R" are H or $C_1$–$C_3$alkyl;

$R_3$ and $R_8$, independently of one another, are $C_1$–$C_4$alkyl, halogen H, OCN or OH, $C_1$–$C_4$alkoxy, alkythio, mercaptan, nitro, —OCOR($C_1$–$C_3$alkyl), —NCOR($C_1$–$C_3$alkyl), —COR, —NO$_2$, —NR'R", wherein R, R' and R" are H or $C_1$–$C_3$alkyl; or $R_1$ and $R_2$ together and/or $R_2$ and $R_3$ together, and/or $R_9$ and $R_{10}$ together, and/or $R_8$ and $R_9$ together, independently of one another, form one or more aromatic rings or five or six membered cycloalkylene that can each be substituted with $C_1$–$C_4$alkyl or halogen;

$R_{11}$ and $R_{12}$, independently of one another are H, phenyl, $C_1$–$C_4$alkyl or halogen;

wherein at least one of aromatic rings A and B or at least one of the aromatic rings or the five or six membered ring formed by $R_1$ and $R_2$ and/or $R_2$ and $R_3$ and/or $R_9$ and $R_{10}$ and/or $R_8$ and $R_9$ is substituted by at least one cyanato group, or a cyclotrimerized reaction product of cyanate esters wherein at least one of said cyanate esters is said compound of formula (I) and with the balance of the composition optionally being at least one of components (b) to (g) as follows:

b) solvent, c) additional mono- and polycyanato-group containing compounds, d) thermal curable or reactive compounds other than cyanate esters, e) cure accelerators f) tougheners and g) customary additives and fillers.

12. A composition comprising a) about 50 to 100% by weight of a compound represented by formula (I):

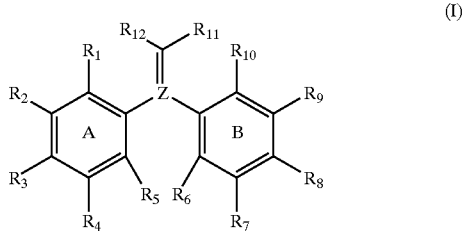

(I)

wherein

Z is $C_1$–$C_4$ alkylene group or a five or six membered cycolalkylene;

$R_1$, $R_5$, $R_6$ and $R_{10}$, independently of one another, are unsubstituted or halogen- or $C_1$–$C_3$alkyl-substituted $C_1$–$C_4$ alkyl that can be saturated or unsaturated, halogen, H, OCN, OH, $C_1$–$C_4$alkoxy, alkythio, mercaptan, nitro, —OCOR($C_1$–$C_3$alkyl), —NCOR ($C_1$–$C_3$alkyl), —COR, —NO$_2$, —NR'R", wherein R, R' and R" are H or $C_1$–$C_3$alkyl;

$R_2$, $R_4$, $R_7$ and $R_9$, independently of one another, are $C_1$–$C_4$alkyl, halogen, H, OCN, or OH, $C_1$–$C_4$alkoxy, alkythio, mercaptan, nitro, —OCOR($C_1$–$C_3$alkyl), —NCOR($C_1$–$C_3$alkyl), —COR, —NO$_2$, —NR'R", wherein R, R' and R" are H or $C_1$–$C_3$alkyl;

$R_3$ and $R_8$, independently of one another, are $C_1$–$C_4$alkyl, halogen H, OCN or OH, $C_1$–$C_4$alkoxy, alkythio, mercaptan, nitro, —OCOR($C_1$–$C_3$alkyl), —NCOR($C_1$–$C_3$alkyl), —COR, —NO$_2$, —NR'R", wherein R, R' and R" are H or $C_1$–$C_3$alkyl; or $R_1$ and $R_2$ together and/or $R_2$ and $R_3$ together, and/or $R_9$ and $R_{10}$ together, and/or $R_8$ and $R_9$ together, independently of one another, form one or more aromatic rings or five or six membered cycloalkylene that can each be substituted with $C_1$–$C_4$alkyl or halogen;

$R_{11}$ and $R_{12}$, independently of one another are H, phenyl, $C_1$–$C_4$alkyl or halogen;

wherein at least one of aromatic rings A and B or at least one of the aromatic rings or the five or six membered ring formed by $R_1$ and $R_2$ and/or $R_2$ and $R_3$ and/or $R_9$ and $R_{10}$ and/or $R_8$ and $R_9$ is substituted by at least one cyanato group, or a cyclotrimerized reaction product of cyanate esters wherein at least one of said cyanate esters is said compound of formula (I) and with the balance of the composition optionally being at least one of components b) to g) as follows:

b) solvent,
c) additional mono- and polycyanato-group containing compounds,
d) thermal curable or reactive compounds other than cyanate esters,
e) cure accelerators
f) tougheners and
g) customary additives and fillers.

13. A composition comprising
a) about 60 to 99% by weight of a compound represented by formula (I):

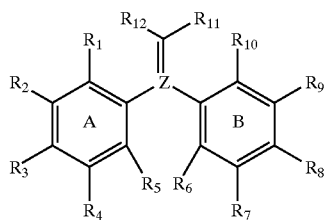

wherein

Z is $C_1$–$C_4$ alkylene group or a five or six membered cycolalkylene;

$R_1$, $R_5$, $R_6$ and $R_{10}$, independently of one another, are unsubstituted or halogen- or $C_1$–$C_3$alkyl-substituted $C_1$–$C_4$ alkyl that can be saturated or unsaturated, halogen, H, OCN, OH, $C_1$–$C_4$alkoxy, alkythio, mercaptan, nitro, —OCOR($C_1$–$C_3$alkyl), —NCOR ($C_1$–$C_3$alkyl), —COR, —NO$_2$, —NR'R", wherein R, R' and R" are H or $C_1$–$C_3$alkyl; $R_2$, $R_4$, $R_7$ and $R_9$, independently of one another, are $C_1$–$C_4$alkyl, halogen, H, OCN, or OH, $C_1$–$C_4$alkoxy, alkythio, mercaptan, nitro, —OCOR($C_1$–$C_3$alkyl), —NCOR ($C_1$–$C_3$alkyl), —COR, —NO$_2$, —NR'R", wherein R, R' and R" are H or $C_1$–$C_3$alkyl;

$R_3$ and $R_8$, independently of one another, are $C_1$–$C_4$alkyl, halogen H, OCN or OH, $C_1$–$C_4$alkoxy, alkythio, mercaptan, nitro, —OCOR($C_1$–$C_3$alkyl), —NCOR($C_1$–$C_3$alkyl), —COR, —NO$_2$, —NR'R", wherein R, R' and R" are H or $C_1$–$C_3$alkyl; or $R_1$ and $R_2$ together and/or $R_2$ and $R_3$ together, and/or $R_9$ and $R_{10}$ together, and/or $R_8$ and $R_9$ together, independently of one another, form one or more aromatic rings or five or six membered cycloalkylene that can each be substituted with $C_1$–$C_4$alkyl or halogen;

$R_{11}$ and $R_{12}$, independently of one another are H, phenyl, $C_1$–$C_4$alkyl or halogen;

wherein at least one of aromatic rings A and B or at least one of the aromatic rings or the five or six membered ring formed by $R_1$ and $R_2$ and/or $R_2$ and $R_3$ and/or $R_9$ and $R_{10}$ and/or $R_8$ and $R_9$ is substituted by at least one cyanato group, or a cyclotrimerized reaction product of cyanate esters wherein at least one of said cyanate esters is said compound of formula (I) and with the balance of the composition being at least one of components b) to g) as follows:

b) solvent,
c) additional mono- and polycyanato-group containing compounds,
d) thermal curable or reactive compounds other than cyanate esters,
e) cure accelerators
f) tougheners and
g) customary additives and fillers.

14. A cured article resulting from a curable mixture comprising a compound represented by formula (I):

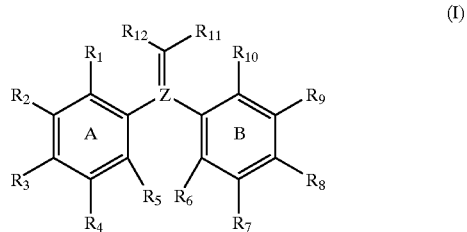

wherein

Z is $C_1$–$C_4$ alkylene group or a five or six membered cycolalkylene;

$R_1$, $R_5$, $R_6$ and $R_{10}$, independently of one another, are unsubstituted or halogen- or $C_1$–$C_3$alkyl-substituted $C_1$–$C_4$ alkyl that can be saturated or unsaturated, halogen, H, OCN, OH, $C_1$–$C_4$alkoxy, alkythio, mercaptan, nitro, —OCOR($C_1$–$C_3$alkyl, —NCOR ($C_1$–$C_3$alkyl), —COR, —NO$_2$, —NR'R", wherein R, R' and R" are H or $C_1$–$C_3$alkyl;

$R_2$, $R_4$, $R_7$ and $R_9$, independently of one another, are $C_1$–$C_4$alkyl, halogen, H, OCN, or OH, $C_1$–$C_4$alkoxy, alkythio, mercaptan, nitro, —OCOR($C_1$–$C_3$alkyl), —NCOR($C_1$–$C_3$alkyl), —COR, —NO$_2$, —NR'R", wherein R, R' and R" are H or $C_1$–$C_3$alkyl;

$R_3$ and $R_8$, independently of one another, are $C_1$–$C_4$alkyl, halogen H, OCN or OH, $C_1$–$C_4$alkoxy, alkythio, mercaptan, nitro, —OCOR($C_1$–$C_3$alkyl), —NCOR ($C_1$–$C_3$alkyl), —COR, —NO$_2$, —NR'R", wherein R, R' and R" are H or $C_1$–$C_3$alkyl; or $R_1$ and $R_2$ together and/or $R_2$ and $R_3$ together, and/or $R_9$ and $R_{10}$ together, and/or $R_8$ and $R_9$ together, independently of one another, form one or more aromatic rings or five or six membered cycloalkylene that can each be substituted with $C_1$–$C_4$alkyl or halogen;

$R_{11}$ and $R_{12}$, independently of one another are H, phenyl, $C_1$–$C_4$alkyl or halogen;

wherein at least one of aromatic rings A and B or at least one of the aromatic rings or the five or six membered ring formed by $R_1$ and $R_2$ and/or $R_2$ and $R_3$ and/or $R_9$ and $R_{10}$ and/or $R_8$ and $R_9$ is substituted by at least one cyanato group, or a cyclotrimerized reaction product thereof having a peak heat release rate of less than about 10 Joule/g-° K as measured using a pyrolysis-combustion flow calorimeter developed by the Federal Aviation Administration.

15. A cured article resulting from a curable mixture comprising a compound represented by formula (I):

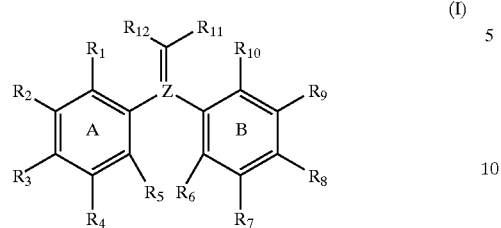

wherein
- Z is $C_1$–$C_4$ alkylene group or a five or six membered cycolalkylene;
- $R_1$, $R_5$, $R_6$ and $R_{10}$, independently of one another, are unsubstituted or halogen- or $C_1$–$C_3$alkyl-substituted $C_1$–$C_4$ alkyl that can be saturated or unsaturated, halogen, H, OCN, OH, $C_1$–$C_4$alkoxy, alkythio, mercaptan, nitro, —OCOR($C_1$–$C_3$alkyl), —NCOR ($C_1$–$C_3$alkyl), —COR, —$NO_2$, —NR'R", wherein R, R' and R" are H or $C_1$–$C_3$alkyl;
- $R_2$, $R_4$, $R_7$ and $R_9$, independently of one another, are $C_1$–$C_4$alkyl, halogen, H, OCN, or OH, $C_1$–$C_4$alkoxy, alkythio, mercaptan, nitro, —OCOR($C_1$–$C_3$alkyl), —NCOR($C_1$–$C_3$alkyl), —COR, —$NO_2$, —NR'R", wherein R, R' and R" are H or $C_1$–$C_3$alkyl;
- $R_3$ and $R_8$ independently of one another, are $C_1$–$C_4$alkyl, halogen H, OCN or OH, $C_1$–$C_4$alkoxy, alkythio, mercaptan, nitro, —OCOR($C_1$–$C_3$alkyl, —NCOR ($C_1$–$C_3$alkyl), —COR, —$NO_2$, —NR'R", wherein R, R' and R" are H or $C_1$–$C_3$alkyl; or
- $R_1$ and $R_2$ together and/or $R_2$ and $R_3$ together, and/or $R_9$ and $R_{10}$ together, and/or $R_8$ and $R_9$ together, independently of one another, form one or more aromatic rings or five or six membered cycloalkylene that can each be substituted with $C_1$–$C_4$alkyl or halogen;
- $R_{11}$ and $R_{12}$, independently of one another are H, phenyl, $C_1$–$C_4$alkyl or halogen;
- wherein at least one of aromatic rings A and B or at least one of the aromatic rings or the five or six membered ring formed by $R_1$ and $R_2$ and/or $R_2$ and $R_3$ and/or $R_9$ and $R_{10}$ and/or $R_8$ and $R_9$ is substituted by at least one cyanato group,
- or a cyclotrimerized reaction product thereof having a peak heat release rate of less than about 25 Joule/g-° K as measured by the Ohio State University heat release test.

16. A cured article resulting from a curable mixture comprising a compound represented by formula (I):

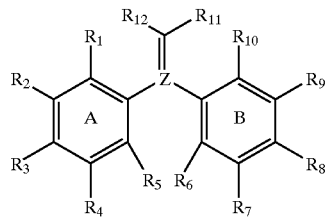

wherein
- Z is $C_1$–$C_4$ alkylene group or a five or six membered cycolalkylene;
- $R_1$, $R_5$, $R_6$ and $R_{10}$, independently of one another, are unsubstituted or halogen- or $C_1$–$C_3$alkyl-substituted $C_1$–$C_4$ alkyl that can be saturated or unsaturated, halogen, H, OCN, OH, $C_1$–$C_4$alkoxy, alkythio, mercaptan, nitro, —OCOR($C_1$–$C_3$alkyl), —NCOR ($C_1$–$C_3$alkyl), —COR, —$NO_2$, —NR'R", wherein R, R' and R" are H or $C_1$–$C_3$alkyl; $R_2$, $R_4$, $R_7$ and $R_9$, independently of one another, are $C_1$–$C_4$alkyl, halogen, H, OCN, or OH, $C_1$–$C_4$alkoxy, alkythio, mercaptan, nitro, —OCOR($C_1$–$C_3$alkyl), —NCOR($C_1$–$C_3$alkyl), —COR, —$NO_2$, —NR'R", wherein R, R' and R" are H or $C_1$–$C_3$alkyl;
- $R_3$ and $R_8$, independently of one another, are $C_1$–$C_4$alkyl, halogen H, OCN or OH, $C_1$–$C_4$alkoxy, alkythio, mercaptan, nitro, —OCOR($C_1$–$C_3$alkyl), —NCOR ($C_1$–$C_3$alkyl), —COR, —$NO_2$, —NR'R", wherein R, R' and R" are H or $C_1$–$C_3$alkyl; or
- $R_1$ and $R_2$ together and/or $R_2$ and $R_3$ together, and/or $R_9$ and $R_{10}$ together, and/or $R_8$ and $R_9$ together, independently of one another, form one or more aromatic rings or five or six membered cycloalkylene that can each be substituted with $C_1$–$C_4$alkyl or halogen;
- $R_{11}$ and $R_{12}$, independently of one another are H, phenyl, $C_1$–$C_4$alkyl or halogen;
- wherein at least one of aromatic rings A and B or at least one of the aromatic rings or the five or six membered ring formed by $R_1$, and $R_2$ and/or $R_2$ and $R_3$ and/or $R_9$ and $R_{10}$ and/or $R_8$ and $R_9$ is substituted by at least one cyanato group, or a cyclotrimerized reaction product thereof having a total heat release of less than about 3 KJoule/g.

* * * * *